United States Patent
McMurtry et al.

(10) Patent No.: US 10,351,945 B2
(45) Date of Patent: Jul. 16, 2019

(54) METHOD FOR OBTAINING A NANO CAPSULE STRUCTURE

(71) Applicants: UNIVERSITE DE LORRAINE, Nancy (FR); CENTRE NATIONAL DE LA RECHERCHE SCIENTIFIQUE, Paris (FR)

(72) Inventors: Stefan McMurtry, Laxou (FR); Omar Elmazria, Seichamps (FR)

(73) Assignees: UNIVERSITE DE LORRAINE, Nancy (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 264 days.

(21) Appl. No.: 14/405,670

(22) PCT Filed: Jun. 13, 2013

(86) PCT No.: PCT/EP2013/062221
§ 371 (c)(1),
(2) Date: Dec. 4, 2014

(87) PCT Pub. No.: WO2013/186292
PCT Pub. Date: Dec. 19, 2013

(65) Prior Publication Data
US 2015/0167146 A1      Jun. 18, 2015

(30) Foreign Application Priority Data
Jun. 14, 2012   (FR) ...................................... 12 55561

(51) Int. Cl.
*C23C 14/34*     (2006.01)
*C23C 14/04*     (2006.01)
(Continued)

(52) U.S. Cl.
CPC ........... *C23C 14/042* (2013.01); *B01J 13/043* (2013.01); *B65D 65/42* (2013.01); *C23C 28/00* (2013.01); *A61K 9/5192* (2013.01)

(58) Field of Classification Search
CPC .............................. C23C 28/00; A61K 9/5192
See application file for complete search history.

(56) References Cited

U.S. PATENT DOCUMENTS

| | | |
|---|---|---|
| 5,893,974 A | 4/1999 | Keller et al. |
| 2003/0029558 A1 | 2/2003 | Hochrainer et al. |

(Continued)

FOREIGN PATENT DOCUMENTS

| | | |
|---|---|---|
| EP | 0512693 A1 | 11/1992 |
| JP | 2011158665 A | 8/2011 |

(Continued)

OTHER PUBLICATIONS

Database WPI Week 201157 Thomson Scientific, London, GB; AN 2011-K50337 XP002726674, & JP 2011 158665 A (Sony Corp) Aug. 18, 2011 (Aug. 18, 2011).

(Continued)

*Primary Examiner* — Jason Berman
(74) *Attorney, Agent, or Firm* — Craft Chu PLLC; Andrew W. Chu (57) ABSTRACT

The method for obtaining a nano-capsule structure includes at least one layer of resin deposited on a layer of substrate. The capsule nanometric in size is capable of enabling the encapsulation of a compound. The layer of resin is structured, by low voltage electron lithography, or by optical lithography or by nanoimprinting in such a way as to obtain at least one cavity in the thickness of the layer of resin. The cavity has a depth smaller than the thickness of the layer of resin. At least one layer of an encapsulating material is isotropically deposited by sputtering the material under (Continued)

vacuum. The cavity is sealed with a sealing material. The layer of resin is dissolved by soaking in a suitable solvent.

16 Claims, 5 Drawing Sheets

(51) Int. Cl.
*B01J 13/04* (2006.01)
*B65D 65/42* (2006.01)
*C23C 28/00* (2006.01)
*A61K 9/51* (2006.01)

(56) References Cited

U.S. PATENT DOCUMENTS

2004/0113543 A1  6/2004  Daniels
2009/0242382 A1  10/2009  Lipinska-Kalita et al.

FOREIGN PATENT DOCUMENTS

KR   100834247 B1   5/2008
WO      9524472 A1   9/1995
WO      0141736 A2   6/2001
WO   2011102809 A1   8/2011

OTHER PUBLICATIONS

Database WPI Week 200902 Thomson Scientific, London, GB; AN 2009-A40396 XP002726675, & KR 100 834 247 B1 (Dongbu Electronics Co Ltd) May 30, 2008 (May 30, 2008).

METHOD FOR OBTAINING A NANO CAPSULE STRUCTURE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention is related to the field of nano-capsule structures.

The present invention may find its application in many fields, because of the particular properties of such structures. By way of an example, the invention will find an application in the field of energy production, or also in the field of encapsulation of compounds, irrespective of the latter being solid, liquid or gaseous, including vacuum, i.e. at a pressure lower than the atmospheric pressure.

The invention relates more particularly to a method for obtaining nano-capsule structures capable of permitting the encapsulation of a compound. Thus, these structures can also be referred to as nano-tanks and permit a physical encapsulation of various compounds in the three common states of material: solid, liquid or gaseous. It is also possible to encapsulate vacuum.

2. Description of Related Art Including Information Disclosed Under 37 CFR 1.97 and 37 CFR 1.98.

Nowadays, the chemical encapsulation of compounds is well known. The methods for chemical encapsulation consist in coating a molecule for the purpose of protecting the latter. The main objective of such methods is to permit a release of the molecule encapsulated in a chemical way, in a particular situation. For example, one may wish to achieve a progressive dissolution of the coating in the gastrointestinal tract, so as to release the active substance it contains.

Thus, from the prior art document WO 2009/039458 is known the encapsulation of microstructures or nanostructures with polymeric gels, more particularly micro-gels. Such structures can namely permit the encapsulation of viruses, whereby the latter can serve as a matrix for the synthesis of nanostructures or microstructures.

From WO 2007/003054 is also known a method for the immobilization of bio-molecules on polymers from natural origin or obtained by chemical synthesis, whereby the latter can be functionalized in the form of nano-particles, in order to permit a bonding of the bio-molecule with the nano-particle. The bonding between bio-molecules and polymer particles, for example the nano-particles, occurs by a chemical reaction that is a cycloaddition. Molecules or therapeutic agents can be encapsulated within particles, so as to namely permit their intravenous delivery.

However, the encapsulation by chemical means has several disadvantages. On the one hand, each type of molecule requires a particular encapsulation; indeed, some molecules are more delicate than other and are likely to be destroyed by the coating solution. Therefore, all molecules cannot be coated by means of chemical encapsulation. On the other hand, this type of encapsulation also has limitations as regards the state of the compound to be encapsulated and the quantity. In particular, the gaseous and liquid compounds cannot be encapsulated by chemical means. In addition, the molecular aggregates can only be encapsulated in the case where the coating solution does not dissolve them. Finally, positioning molecules encapsulated by chemical means on a substrate is particularly difficult, which limits the possible fields of application.

The methods consisting in coating a compound by chemical means have some limitations and are not entirely satisfactory.

From WO 2011/102809 is also known a method for encapsulation by chemical means, which attempts to cope with the above drawbacks, in particular by permitting an encapsulation of liquid, solid, or gaseous compounds.

This document relates to a method for obtaining a plurality of micro-chambers. In a first step of this method, a network of micro-wells is printed by nanoimprinting or electron lithography on a polymer substrate. In a second step, a first layer, also of polymer, is applied on this structured substrate.

This first layer consists in particular of a succession of bi-layers, at least 10, each including two differently charged layers. In other words, each bi-layer includes a layer of anionic polymer and a layer of cationic polymer.

Any compound whatsoever is then charged into the micro-wells, then a sealing layer is applied.

The layer-by-layer deposition onto the substrate occurs by soaking the substrate in the different polymer solutions or by implementing a sputtering technique. Such a technique, referred to as "spray coating" in English, is adapted for the deposition of polymers in liquid phase and consists of a propelling, by means of an airflow, of said polymer dissolved in a solvent.

However, the method described in this document still has a number of drawbacks.

In particular, the techniques for depositing the first layer are inaccurate and the polymeric materials being used are not suitable for obtaining an encapsulating layer of a perfectly controlled thickness, while being extremely thin and particularly resistant; therefore, the method only permits to obtain a matrix of micro-chambers, and no isolated structures, and the so obtained matrix does not permit to release each of the micro-chambers independently from each other, without causing the de-structuring of this polymer layer. It is also observed that, since the substrate as well as the first layer are made of polymeric material, the problem of the separation of the micro-chambers from the substrate arises. In any case, this requires the selection of specific polymers, on the one hand, for the substrate and, on the other hand, for said first layer.

In addition, it is difficult to obtain structures of a very small size, in the range of one nanometer, by the implementation of the process steps described in that document. Indeed, the deposition of the first layer by soaking in a solution, or by another cited technique, does not permit an optimal penetration of said solution into a cavity that would have nanometric dimensions, because of capillary and tension forces existing between the first layer and the substrate.

Now, the obtaining of individualized structures nanometric in size is of a particular interest in many fields of application, and namely in the medical field.

Finally, the method described in that document is cumbersome and time-consuming to be implemented. Indeed, besides the plurality of operations of soaking in various polymer solutions necessary to obtain the product, a sonication of the substrate has to be carried out in order to remove the air bubbles likely to cause the formation of a discontinuous and non-uniform layer during the soaking operations.

The inventors have therefore tried to develop a technique permitting to cope with the drawbacks of the chemical encapsulation techniques, and permitting to obtain nano-capsule structures that can namely result into a physical encapsulation of compounds.

As regards the physical techniques, from the state of the art is namely known a method referred to as "lift off", which permits to structure a resin generally deposited on a substrate. More particularly, the lift-off consists in printing, in a layer of resin deposited at the surface of a substrate, a reverse pattern by electron or optical lithography. A thin metal layer is then deposited by evaporation, so as to try to cover the remaining resin and the portions of the substrate from which the resin has been removed by lithography. Finally, the remaining resin is removed, for example by dissolution, so as to keep only the metal layer that is into contact with the substrate.

Thus, by proceeding to a lithography step, followed by a metal deposition through evaporation and a lift-off of the resin, it is for example possible to obtain a structuring of gold pads on silicon.

From patent document WO 2007/072247 is also known a particular lift-off method, in which a cap-shaped profile is formed in order to permit to obtain a metal layer having a predetermined lateral shape, at a predetermined position of a surface of a semiconductor material. In the same way as the above-cited technique, it only permits to structure pads on the surface of a layer of substrate.

The techniques presently existing in the field of structuring of surfaces thus permit only to obtain monolithic structures, such as pads, and not hollow structures, including thin walls aimed at permitting the encapsulation of compounds, irrespective of same being liquid, solid, or gaseous.

In addition, the technique of deposition of a metal by evaporation is not fully satisfactory. Indeed, there are difficulties in obtaining a continuous, or isotropic, metal layer on the surface of a resin. Furthermore, the techniques for structuring resin are not entirely suitable, and lead to a perforation of the resin, resulting in additional difficulties in the manufacture of closed structures.

SUMMARY OF THE INVENTION

The invention provides the possibility of coping with the numerous drawbacks of the state of the art by providing an original method for obtaining nano-capsule structure having any shape, including a thin and continuous layer of at least one material forming said structures, which, as the case may be, facilitates the separation into individual nano-capsules.

Furthermore, these nano-capsules are likely to encapsulate a solid, liquid or gaseous compound, including vacuum.

To this end, the present invention relates to a method for obtaining a nano-capsule structure including at least one capsule nanometric in size, said method including the following steps:
  at least one layer of resin is deposited on a layer of substrate;
  said layer of resin is structured, by low-voltage electron lithography, or by optical lithography or nanoimprinting, so as to obtain at least one cavity in the thickness of said layer of resin, said cavity having a depth p smaller than the thickness E of said layer of resin;
  an isotropic deposition of at least one layer of an encapsulating material is carried out by sputtering under vacuum of said material;
  the cavity or cavities are sealed with a sealing material;
  the layer of resin is dissolved by soaking into a suitable solvent.

Preferably, the method according to the present invention permits to obtain a nano-capsule structure capable of permitting to encapsulate a compound.

By isotropic deposition is understood a deposition of a thin layer, preferably formed of a metallic, semiconductor, insulating or piezoelectric material, and which is continuous on the entire resin. In particular, the method according to the present invention permits to deposit a thin layer of metallic, piezoelectric semiconductor or insulating material on the entire layer of resin and in the cavities formed therein, the side walls of said cavities being also covered by the deposited material, thanks to the step of sputtering deposition under vacuum.

An isotropic deposition is opposed to an anisotropic deposition, obtained by the implementation of the presently used techniques, for which areas with no deposition remain, which are not covered by the material.

According to further features of the invention:
  following the step of isotropic deposition of at least one layer of an encapsulating material by sputtering under vacuum, the cavity or cavities of a compound of any kind are filled, whereby said compound can be liquid, solid or gaseous, including vacuum;
  the layer of resin is structured by low-voltage electron lithography, the latter being between 1 and 15 kV; prior to the structuring of the layer of resin by electron lithography, it is possible to perform an iterative approach test, in order to determine the electron dose to be sent onto the layer of resin, so as to avoid a piercing of said layer of resin until reaching the layer of substrate;
  a layer of resin having a thickness E between 300 nm and 2 µm is deposited by spin coating and said layer of resin is structured so as to obtain a cavity having a depth p between 20 nm and 1 µm, preferably between 50 and 500 nm, preferably between 50 and 300 nm, said depth p being smaller than said thickness E;
  the isotropic deposition by sputtering under vacuum of encapsulating material is carried out at a power between 80 and 120 Watts, preferably equal to 100 W;
  all the steps of said method are performed at a controlled temperature between 15° C. and 30° C., preferably between 18 and 25° C., preferably equal to 20° C.;
  at least one layer of encapsulating material, the thickness e of which is between 10 and 200 nm, is sprayed;
  a layer of resin comprised of polymethyl methacrylate and/or polymethyl methacrylate methacrylic acid is deposited;
  the substrate is formed of a flexible or rigid material selected among silicon, zinc oxide, aluminum nitride, silicon oxide, aluminum oxide, polymers, plastic materials;
  a sprayable encapsulating material selected among metallic materials, semiconductor materials, piezoelectric materials and insulating materials is deposited;
  the cavity or cavities are sealed with a sealing material selected among polymers, metals, epoxy resins and biocompatible resins, said sealing material being capable of withstanding the solvent used in the step of dissolution of the resin;

prior to the step of dissolving the layer of resin, the nano-capsule structure is transferred onto a second substrate by applying an adhesive resin on the surface of the sealing material, then a second substrate is deposited onto said adhesive resin; the nano-capsule structure can also be transferred onto a second substrate by depositing said second substrate on the surface of the sealing material, the latter then forming an adhesive resin for transferring the nano-capsule structure onto a second substrate;

following the step of transferring the nano-capsule structure onto a second substrate, a sputtering under vacuum of at least one second layer of a metal or insulating or semiconductor or piezoelectric material onto the layer of encapsulating material is carried out;

following the obtaining of the nono-capsule structure by sealing the cavity or cavities with a sealing material, the method also includes the following steps:

the sealing material layer is structured, through alignment with the first structuring of the layer of resin, by electron lithography or optical lithography or nanoimprinting, so as to remove said material, except at the level of the nano-capsule(s), which remain sealed;

the layer of encapsulating material is removed by chemical etching or by soaking or by reactive ion etching or ion beam etching;

after the dissolution of the layer of resin by soaking in a suitable solvent, said nano-capsule(s) are released in solution.

The present invention also relates to a nano-capsule structure including at least one capsule nanometric in size adapted to permit the encapsulation of a compound and formed by a container of a given depth p and having an opening sealed by a seal formed of the sealing material, the container comprising a cover including at least one layer of an encapsulating material, the thickness e of which fulfils the following ratio: p/e larger than 2, preferably larger than 6 and preferably larger than 10.

The invention also relates to the use of at least one nano-capsule structure for the encapsulation of a compound of any kind.

Preferably, a nano-capsule structure according to the invention can be used for the release of the compound on command, by applying a means permitting the destruction of the cover of the nano-capsule(s) of said structure.

The invention also relates to the use of the nano-capsule structure for generating electricity or for manufacturing an acoustic wave nano-resonator or for manufacturing a photodiode or for manufacturing an omnidirectional optical source.

The present invention includes many advantages. On the one hand, the method according to the invention is easy to be implemented, and does not require too large a number of steps. On the other hand, it permits to obtain nano-capsule structures including at least one closed and internally hollow nano-capsule, so as to permit the eventual filling of the capsule with any compound whatsoever.

In particular, such a compound can consist of a drug-type active substance, and the present invention permits to encapsulate such an active substance, so as to favor a controlled release of the latter.

The method according to the present invention, and the nano-capsule structure deriving from same, can permit the incorporation of a compound of any physical nature (solid, liquid or gaseous, including vacuum), unlike the existing chemical structures, which namely do not permit an encapsulation of molecules in the gaseous state or in the liquid state.

Finally, the present method permits, in a novel way, to obtain a nano-capsule structure having a thin and strong layer of an encapsulating material, whereby said structure can permit the encapsulation of a compound and the individual release of the nano-capsules. Moreover, these nano-capsule structures are likely to be used in varied fields of applications, for example in medicine or in the field of energy production.

Further features and advantages of the invention will become clear from the following detailed description of non-restrictive embodiments of the invention, with reference to the attached figures.

DETAILED DESCRIPTION OF THE DRAWINGS

Figure 1:
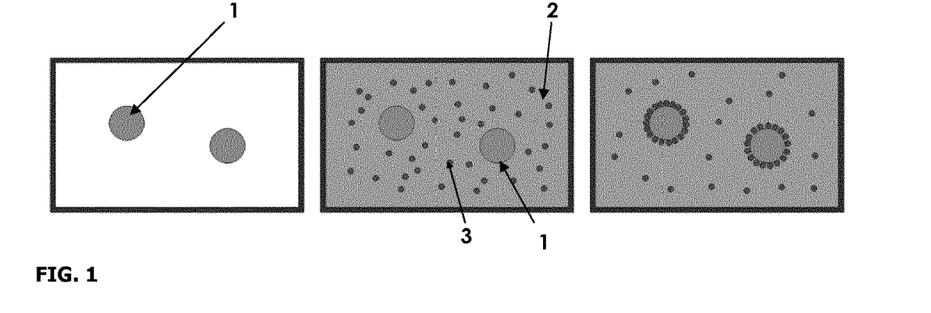
FIG. 1 is a schematic view, showing the steps of the known method for chemical encapsulation.

FIG. 1 schematically illustrates one of the techniques used in the prior art for chemically encapsulating molecules, e.g.

active drug substances. The molecules 1 that must be encapsulated can be brought into the presence of a coating solution 2 including a coating material 3, such as a polymer having an affinity for the molecule 1 to be encapsulated.

As mentioned above, some techniques for encapsulation by a chemical process have the drawback of not permitting an encapsulation of liquid or gaseous compounds and especially of making it almost impossible to obtain, in a reproducible and controlled way, structures the dimensions of which are in the range of one nanometer.

Figure 2:
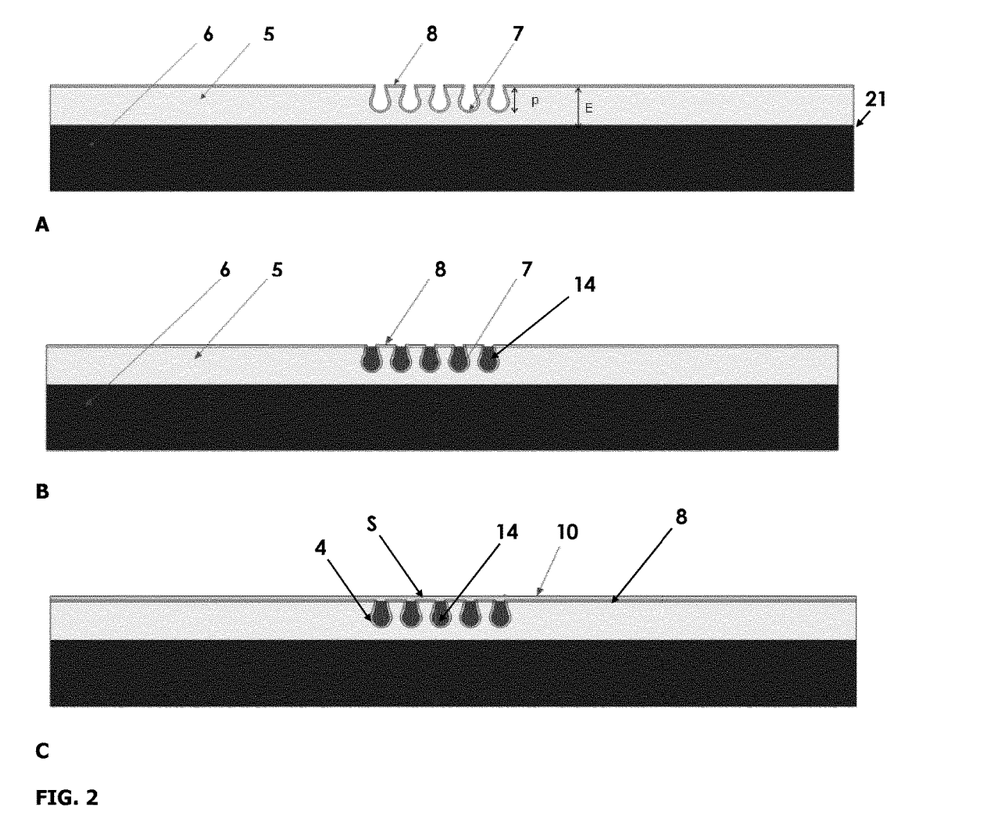
FIGS. 2A to 2C are schematic views, illustrating the steps of the method according to the present invention for obtaining a nano-capsule structure.

In order to cope therewith, the present invention relates to a method permitting to obtain a nano-capsule 4 structure S, including at least one capsule 4 nanometric in size, namely capable of permitting an encapsulation of a compound, and preferably a plurality of nano-capsules 4, as shown namely in FIG. 2C.

Thus, a structure S including one single nano-capsule 4 corresponds to an individual nano-capsule 4.

The individual nano-capsule 4 can also be obtained from a structure S including a plurality of nano-capsules 4 separated from each other by a suitable means.

More particularly, the method according to the invention, schematically shown in FIGS. 2A, 2B and 2C, includes a step of depositing at least one layer of resin 5 on a layer of substrate 6, followed by a step in which said layer of resin 5 is structured by low-voltage electron lithography or optical lithography or nanoimprinting, in order to obtain the formation of cavities 7 in the thickness of this layer 5. In a particularly advantageous way, the cavity 7 has a depth p smaller than the thickness E of the layer of resin 5, so as not to fully perforate the thickness of the layer of resin 5.

Thereafter, as shown in FIG. 2A, a deposition of at least one layer of an encapsulating material 8 is formed on the entire surface of the resin 5 by sputtering under vacuum, using equipment for sputtering under vacuum.

Such a deposit is referred to as "isotropic" deposition. In other words, this means that the deposition is continuous over the entire surface of the layer of resin 5, namely at the level of the side walls and the bottom of the cavities 7 resulting from the step of structuring the resin 5, as well as on the remainder of the resin 5 that has not been structured.

The cavity or cavities 7 covered with encapsulating material 8 can then advantageously be filled with any compound 14 that one wants to encapsulate, as shown in FIG. 2B. Said compound 14 can be either in liquid, gaseous, or solid state. The encapsulated compound can also consist of vacuum the pressure of which is lower than the atmospheric pressure. Such an operation is carried out by deposition of said compound 14 in the cavity 7, by any means known to the specialist in the art and suitable for this purpose.

The cavity or cavities 7, now including eventually but not necessarily, a suitable compound 14 are then sealed by means of a sealing material 10, the latter being deposited on the entire surface, on top of the encapsulating material layer 8 and above the cavities 7 optionally containing the compound 14. This step of the method is illustrated in the attached FIG. 2C.

Once this operation has been performed, in the layer of resin 5 is obtained a nano-capsule 4 structure S capable of permitting the encapsulation of a compound, and preferably including a plurality of nano-capsules 4. Such a nano-capsule 4 structure S can also be referred to as a nano-tank or nano-tanks, whereby said nano-capsule 4 structure S is sealed and can contain, within the capsule 4, a compound 14 to be encapsulated.

Thereafter, the layer of resin 5 is dissolved by soaking the latter in a suitable solvent.

The nano-capsules 4 of the structure S of a nano-capsule can then be released from said resin 5. When a structure S including several nano-capsules 4 has been obtained by the method according to the invention, it is possible to separate said capsules 4 by stirring; thus individual nano-capsules 4 can be obtained in solution, the latter advantageously including any compound 14 therein.

A particular embodiment, also permitting to obtain nano-capsules 4 in solution is illustrated in FIGS. 3A to 3D.

Figure 3:
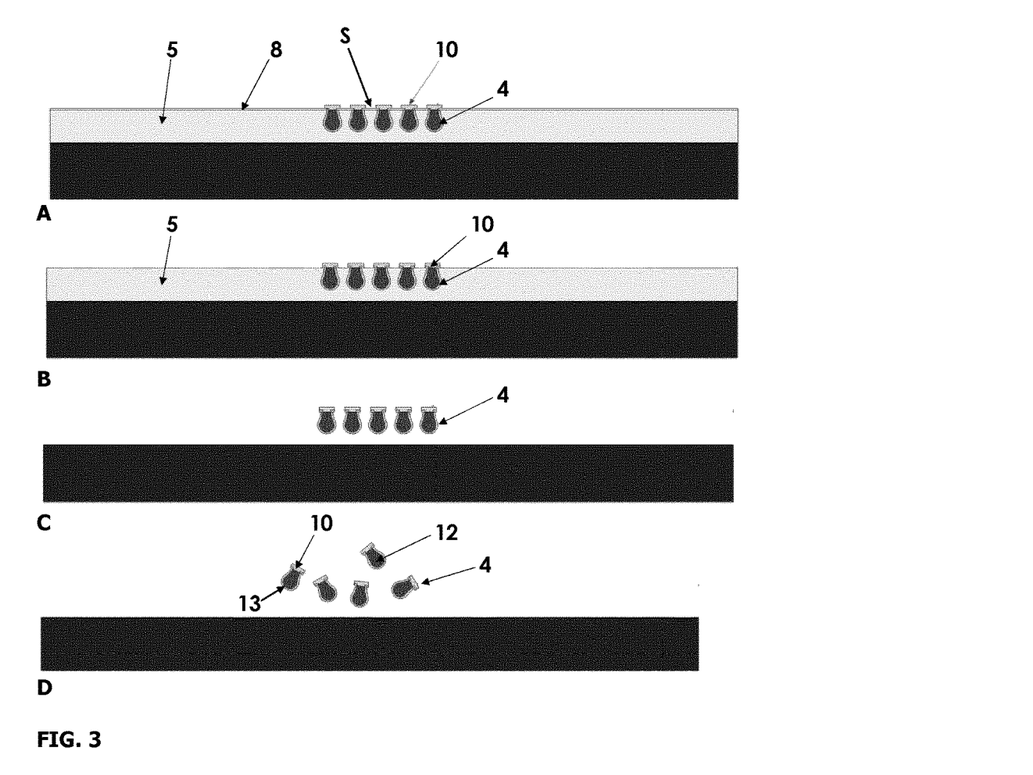
FIGS. 3A to 3D show schematic views of a particular embodiment for the release of nano-capsules.

In this embodiment, after the deposition of a layer of sealing material 10, this layer is preferably structured by the electron lithography technique; however, the optical lithography or nanoimprinting techniques can also be implemented for the structuring of the layer of sealing material 10. Irrespective of the technique implemented for structuring the layer of sealing material 10, the latter is aligned with the first lithography that allows the structuring of the layer of resin 5, so as to remove said material 10 from the entire surface of said resin 5, except at the level of the capsules 4 that remain sealed.

The result is visible in FIG. 3A: a nano-capsule 4 structure S is obtained that includes a plurality of nano-capsules 4 capable of permitting the encapsulation of a compound and sealed with the sealing material 10, the latter having been removed from the rest of the surface.

The encapsulating material 8, visible in FIG. 3A, is then removed from the surface of the resin 5, preferably by the chemical etching technique, or by soaking, or by ion beam etching (IBE) or by reactive ion etching (RIE). These techniques permit a dissolution of the encapsulating material 8, as shown in FIG. 3B. The remaining sealing material 10 is, in turn, preserved.

The resin 5 is then dissolved by the action of a suitable solvent, as shown in FIG. 3C, which permits a release of the individual nano-capsules 4 in solution. This step is illustrated in FIG. 3D. The released nano-capsules 4 comprise at least one capsule formed of a container 12 of a given depth p equivalent to that of the cavity 7. Said container 12 includes a cover 13, formed by at least one layer of encapsulating material 8, and has an opening closed by a seal formed by the sealing material 10. The nano-capsules 4 can also include any compound 14 encapsulated in said capsules 4.

Figure 4:
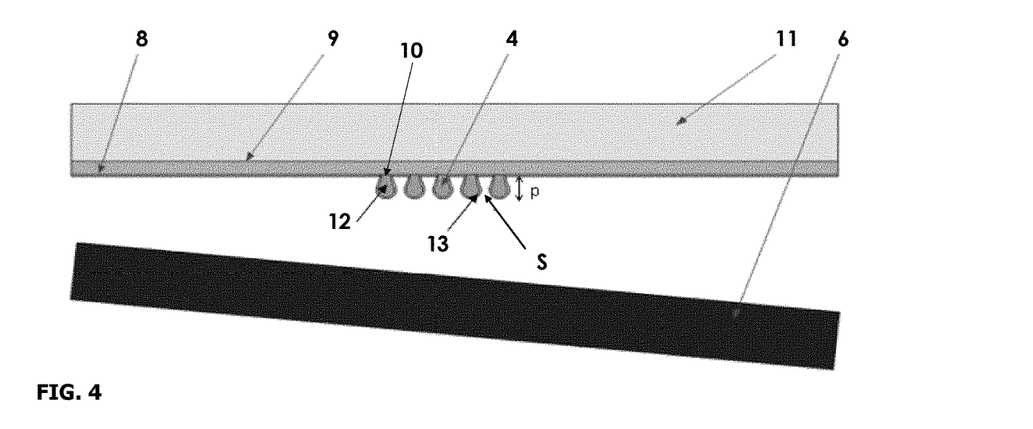
FIG. 4 is a schematic view, illustrating an embodiment of one of the steps of the method according to the invention, wherein the nano-capsule structure is transferred by bonding to a second substrate.

It is also possible, according to a particular embodiment of the present method shown in FIG. 4, to transfer the nano-capsule 4 structure S capable of encapsulating a compound onto a second substrate 11, prior to the dissolution of the layer of resin 5 in a solvent.

According to an embodiment, in order to transfer the nano-capsule 4 structure S, eventually encapsulating a compound 14, onto a second substrate 11, an adhesive resin 9 can be deposited on top of the layer of sealing material 10.

According to another embodiment, the adhesive resin 9 can be deposited directly onto the encapsulating material 8. In this case, the adhesive resin 9 also carries out the function of sealing material 10.

In some cases, the layer of sealing material 10 can also be used for bonding during the transfer of the nano-capsule 4 structure S onto a second substrate 11. It is therefore understood that in the case of a transfer of said nano-capsule 4 structure S onto a second substrate 11 the layer of sealing material 10 can form the adhesive resin 9.

Thus, the bonding is obtained by the deposition of the second substrate 11 on the adhesive resin 9 or directly on the layer of sealing material 10 and eventually by applying a light pressing.

Figure 5:
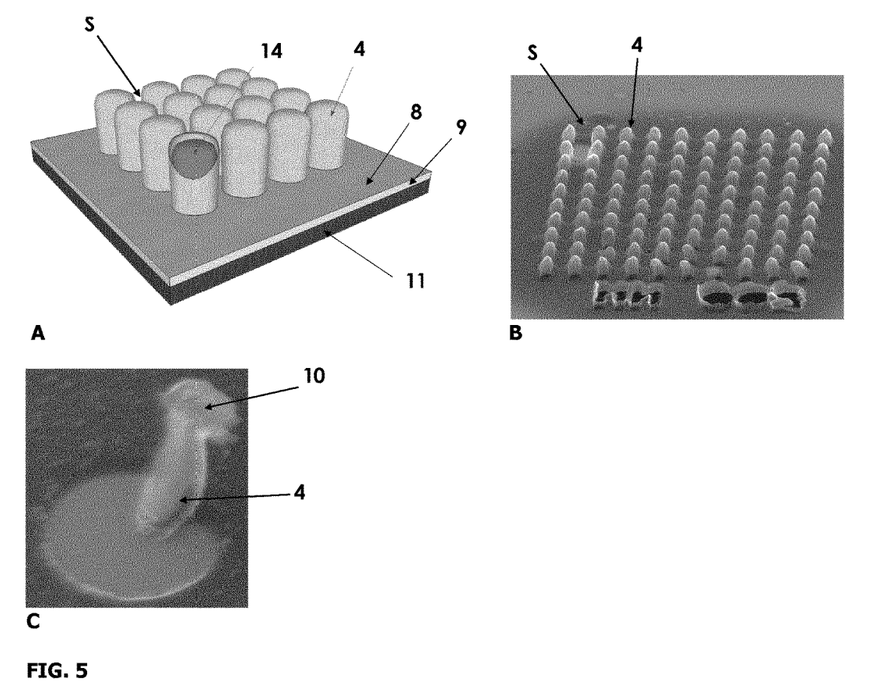
FIG. 5A is a schematic view, showing a nano-capsule structure capable of permitting the encapsulation of a compound.
FIG. 5B corresponds to a photographic view of the structure according to the invention including a plurality of nano-capsules; said nano-capsules have a diameter of 300 nm and are observed with a scanning electron microscope with a magnification of 13,000.
FIG. 5C corresponds to photographic view of an individual nano-capsule sealed with a sealing material such as a SU8 resin, and seen by means of a scanning electron microscope with a magnification of 40,000.

In the case of a transfer of the nano-capsule 4 structure S, capable of permitting the encapsulation of a compound, onto a second substrate 11, the structures S as shown in the attached FIGS. 5A and 5B, i.e. associated with a second substrate 11 shown in FIG. 5A, are obtained. At the level of this figure, the compound 14, eventually encapsulated in the nano-capsule 4 structure S, is also illustrated schematically.

Turning back now to the layer of substrate 6, on which the resin 5 is deposited during the first step of the method according to the invention, the latter can be formed of all kinds of materials, whether rigid or not.

Said layer of substrate 6 can for example be made of a semiconductor material, such as silicon (Si), zinc oxide (ZnO), aluminum nitride (AlN).

The substrate 6 can also consist of an insulating material selected namely among silicon oxide (SiO), aluminum oxide ($Al_2O_3$) or glass.

The substrate 6 can also be formed of a preferably flexible plastic material, such as for example polymethyl methacrylate, or also of a polymer.

The use of a layer of substrate 6, the latter having advantageously a perfectly flat surface, permits an accurate deposition uniform in thickness of a layer of resin 5 that then also has an optimal flatness and uniformity. This guarantees, in the continuation of the method according to the invention, an excellent reproducibility during the structuring of a resin 5, namely when the latter has a large surface, as well as a careful control of the size of the nano-capsules 4 of the structure S obtained during the implementation of the method according to the invention.

Indeed, the use of resin plates, which would not be perfectly flat and which would have a roughness in the range of one micron, does not permit to accurately control the size of the capsules, nor to obtain capsules the size of which is smaller than one micron.

The deposition of the resin 5 on the layer of substrate 6 advantageously occurs by means of the spin coating technique, also referred to as "spin coating" in English.

In this technique, the layer of substrate 6 is placed and held by vacuum on a tray, which rotates at a high and constant speed, in order to permit a spreading of the deposited material, in this case the resin 5, in a perfectly uniform and controlled way, under the action of the centrifugal force.

As regards now this resin 5, which is deposited on the layer of substrate 6, it is preferably formed of polymethyl methacrylate (PMMA) and/or polymethyl methacrylate methacrylic acid) (PMMA-MA). These compounds are transparent thermoplastics; more particularly, PMMA is a transparent methylmethacrylate polymer, also known as Plexiglas™, and which has a low resistance to solvents.

However, this embodiment should not be understood as limiting the invention; indeed, the layer of resin 5 can also consist of any electro-sensitive resins that are dissolved by a solvent and that does not dissolve the adhesive resin 9, and namely when a step of transferring structures 4 onto a second substrate 11 is implemented.

One of the important points of the method according to the invention resides in that the cavities 7, obtained during the step of structuring said resin 5, must have a depth p smaller than the thickness E of the layer of resin 5, so as not to pierce said layer of resin 5 and to facilitate afterwards the release of the nano-capsule 4 structure S by dissolving the resin 5.

Thus, several techniques can be used for structuring the layer of resin 5; preferably, the step of structuring the resin 5 is carried out either by electron lithography or by optical lithography or nanoimprinting.

According to a particularly preferred embodiment of the method according to the invention, the structuring of the layer of resin 5 is carried out using the electron lithography technique. Even more preferably, this technique is implemented under particular conditions, so as to closely control the formation of the cavities 7.

Thus, advantageously, the electron lithography is implemented at low voltage, for example between 1 and 15 kV, with respect to acceleration voltages, which are usually used in electron lithography (higher than 30 kV) for structuring a resin and obtaining cavities having dimensions in the range of one nanometer. A low acceleration voltage is particularly advantageous for controlling the penetration of the electron beam into the layer of resin 5 and, hence, the depth p of the cavity or cavities 7 in the thickness E of said resin 5, so that the cavity or cavities 7 do not reach the layer of substrate 6.

The inventors have also demonstrated that a low acceleration voltage of the electron beam, combined with an adequate thickness of the layer of resin 5, permitted to facilitate, in a particularly interesting way, the control of the penetration of the electrons into said resin 5. In this way, it is even easier to obtain cavities 7 that do not reach the layer of substrate 6. Indeed, in the event the depth p of the cavity 7 would correspond to the thickness E of the resin 5, it would prove extremely difficult, once the encapsulating material 8 and the sealing material 10 have been deposited, to separate the nano-capsules 4 from the structure S, the latter being then connected to the layer of substrate 6.

Preferably, the layer of resin 5 has a thickness E between 300 nm and a few microns, e.g. 2 μm and the depth p of the cavities 7 is between 20 nm and 1 μm, preferably between 50 nm and 500 nm and even more preferably between 50 and 300 nm.

However, such an embodiment is not restrictive of the invention, and the layer of resin 5 can have any thickness E, provided the cavity 7, obtained during the step of structuring said resin 5, has a depth p smaller than said thickness E.

During the structuring of the layer of resin 5 by the electron lithography technique, the electron dose sent onto said resin 5 is also an important parameter in order to avoid structuring this resin 5 down to the layer of substrate 6, in other words, in order to avoid a perforation of the layer of resin 5 down to the layer of substrate 6. However, the electron dose that can be sent at the time of structuring depends namely on the constitution of the layer of resin 5, the density of the cavities 7 at the level of the resin 5 and the dimensions of said cavities 7.

Thus, interestingly, prior to the step of structuring by electron lithography, an iterative approach test is carried out in order to determine the electron dose that can be sent onto the layer of resin 5, so as to avoid piercing said layer of resin 5 down to the layer of substrate 6.

To this end, it is namely possible to use a method referred to as "dose variation" starting from two extreme values that have previously been estimated, an increasing amount of electrons is sent onto the layer of resin 5. After a step of transfer onto a second substrate 11, one observes with a scanning electron microscope if the obtained capsules 4 have been deteriorated or not, depending on the dose of electrons received. If they are effectively damaged, this means that the electron dose sent at the time of the of electron lithography step is too large and that the total thickness E of the layer of resin 5 has been perforated.

Preferably, the electron dose that can be sent at the time of structuring of the layer of resin 5 by electron lithography is smaller than or equal to 250 µC/cm$^2$, preferably smaller than 150 µC/cm$^2$.

Once the cavities 7 have been drilled into the layer of resin 5, the isotropic deposition of at least one layer of encapsulating material 8 on the entire surface of said layer of resin 5 is performed. Advantageously, such an isotropic deposition is performed by spraying.

More specifically, the spraying technique used in the method 15 of the invention is sputtering, which is carried out under vacuum.

Sputtering is a technique that permits the synthesis of materials, from the condensation of a metal vapor from a solid source, on a substrate.

The applicants have demonstrated that such a technique permitted the isotropic deposition of at least one thin layer having a controlled thickness of metallic or semi-conductive or piezoelectric material as encapsulating material 8.

The entire difficulty to be coped with in order to be able to carry out an isotropic deposition of encapsulating material 8 resided indeed in covering uniformly and continuously the entire surface of the cavity 7, and namely the reversed sides, or side walls, of the latter. In addition, an exposure of the layer of resin 5 to the electrons and the photons during the spraying step is likely to degrade said resin 5. As a result, the period of time during which the resin 5 is exposed to the electrons should be reduced, typically to less than 5 min, and preferably to less than 1 min.

The alteration of the layer of resin 5 by irradiation of the latter by photons and/or electrons can be problematic, because it affects the subsequent step of dissolving said resin 5, permitting the release of the nano-capsule 4 structure S or of the very nano-capsules 4. Indeed, when the layer of resin 5 is altered, its dissolution by soaking in a solvent is no longer possible and it is then necessary to proceed to an ultrasonic treatment. However, such a treatment has the disadvantage of damaging the nano-capsule 4 structure S and should therefore preferably be avoided.

Therefore, in order to avoid an alteration of the layer of resin 5 during the step of sputtering under vacuum, the latter is preferably carried out under moderate power, between 80 and 120 Watts, and even more preferably in the range of 100 W. In particular, a moderate power is applied, when a layer of metal material is sprayed.

It is also advantageous to spray the encapsulating material 8 far enough away from the sample 21, shown in FIG. 2A, including the layer of substrate 6 and the resin 5. In addition, said sample 21 should also be protected from any particulate contamination, namely by electrons and/or photons, before or after the deposition of encapsulating material 8. Advantageously, in order to cope with the risk of contamination, a blinding set of a sufficient size can be placed, which permits to avoid any isolation on the resin 5, namely during the adjustment of the plasma of the spraying.

During the implementation of the method according to the invention, the layer of resin 5 is also likely to suffer from degradation, due to a local rise in temperature, which would also make difficult the subsequent dissolution of said resin 5 by a solvent; thus, preferably, the temperature at which the resin 5 is exposed is controlled throughout the method. More preferably, the temperature is maintained between 15° C. and 30° C., preferably between 18 and 25° C., and typically at about 20° C.

The application of these particular conditions greatly facilitates the deposition of material encapsulating 8; it is thus possible to obtain at least one thin cover of this encapsulating material 8 on the entire surface of the resin 5, and namely on the reverse sides of the cavity 7. By applying the method according to the invention, the thickness e of a layer of encapsulating material 8 can be strictly controlled, and it is then possible to obtain a layer nanometric in size, the thickness of which is typically between 10 and 200 nm.

It is also possible to spray several layers of encapsulating material 8, each of the layers then having a controlled thickness between 10 and 200 nm.

As regards the encapsulating material 8, it can consist of any type of sprayable material.

Preferably, said encapsulating material 8 is selected among the metallic materials, such as aluminum (Al), platinum (Pt), tantalum (Ta), gold (Au). The encapsulating material 8 can also be selected among the semiconductor materials, such as silicon (Si), germanium (Ge), indium phosphide (InP), or also the piezoelectric materials, such as namely aluminum nitride (AlN), zinc oxide (ZnO), gallium nitride (GaN), lithium tantalate (LiTaO$_3$), potassium niobate (KnbO$_3$) or also lithium niobate (LiNbO$_3$); the piezoelectric materials have namely the property of deforming when they are subjected to an electric field. Therefore, a nano-capsule 4 structure S obtained from a piezoelectric encapsulating material 8 can be broken by the application of an electric field and thus release the compound 14 eventually encapsulated inside the cavity 7.

Finally, the encapsulating material 8 can consist of an insulating material, such as namely silicon oxide (SiO$_2$), silicon nitride (Si$_3$N$_4$) or alumina (Al$_2$O$_3$) or also glass.

Gold, platinum and tantalum are particularly interesting, because they are considered as biocompatible materials. Referred to as "biocompatible" is a material that does not interfere and does not degrade the biological environment, which it is used in.

Advantageously, in the method according to the invention, several layers that each include an encapsulating material can be sprayed successively.

Thus, it is advantageous to spray, in a first phase, into the cavity 7 a layer 8 of a metallic material, namely Al, Pt, Ta, Si or Au, and then, in a second phase, a layer of piezoelectric material (ZnO, AlN, GaN, LiTaO$_3$, KNbO$_3$, LiNbO$_3$) and, finally, a third layer of metal material as defined above.

Such a sequence of spraying permits to manufacture for example a nano-capsule 4 structure S having a cover 13 including a layer of a piezoelectric material, surrounded by two layers of metallic material, said nano-capsule 4 structure S then being capable of generating electrical energy by interaction between the metal and the piezoelectric material, this energy being likely to be recovered.

Once the step of deposition by spraying of at least one layer of an encapsulating material 8 is completed, each of the cavities 7 can advantageously be filled with a compound 14, namely shown in FIG. 2B, which can be solid, liquid or gaseous. The cavity 7 can also be filled with vacuum, the pressure of which is lower than atmospheric pressure.

The cavity or cavities 7 are then sealed by means of a sealing material 10, the latter permitting to seal said cavity or cavities 7, in order to obtain a nano-capsule 4 structure S incorporating said compound 14.

The sealing material 10 can be of any composition, namely flexible or rigid. It can thus be of a composition identical to or different from that of the encapsulating material 8 or of the adhesive resin 9.

The sealing material 10 can advantageously consist of a polymer or a metal, or also of an epoxy resin. It is however preferable that said sealing material 10 is resistant to the solvent that is used during the step of dissolving the layer of resin 5. Indeed, it is easily understood that, when this is not the case, it is impossible to obtain a structure S the nano-capsules 4 of which are closed.

In addition, it is also advantageous for the sealing material 10 used in the method according to the invention to permit a bonding of the nano-capsule 4 structure S on a second substrate 11, namely in the case a step of transferring said nano-capsule 4 structure S onto a second substrate 11 is proceeded to. When the sealing material 10 permits the bonding during the transfer step, then the deposition of an additional bonding resin 9 is not necessary. In this case, the sealing material 10 forms the adhesive resin permitting the transfer of the nano-capsule 4 structure S onto a second substrate 11.

Said sealing material 10 can preferably consist of a biocompatible resin, namely the SU8 photosensitive resin formed of an epoxy-like viscous polymer.

Such a SU8 resin used as sealing material 10 is particularly advantageous; on the one hand, as mentioned above, the SU8 resin is biocompatible, which permits to use it for manufacturing nano-capsule 4 structures S for biomedical applications. On the other hand, such a SU8 resin can be used at the time of bonding during the transfer of the nano-capsule 4 structure S onto a second substrate 11. The use of the SU8 thus permits to avoid the deposition of a resin specifically for permitting the bonding at the time of the transfer; the SU8 resin has namely been used during the obtaining of the nano-capsule 4 structure S visible in FIG. 5B and the individual nano-capsule 4 of FIG. 5C.

The deposition of said sealing material 10, which can namely consist of a SU8 type biocompatible resin, can be performed by any means known to the specialist of the art and suitable for this purpose.

Preferably, this deposition can be performed by the spin coating technique, as mentioned above.

According to another embodiment, the deposition of the sealing material 10 is performed by the spraying technique, also referred to as "spray coating": this technique implements a projection system using a carrier gas in order to accelerate and to transfer fine particles of the sealing material 10 to the desired location.

Another technique that can be used is soaking, also known as "dip coating". This technique consists in shaping a structured layer by soaking the assembly including the substrate 6 and the resin 5, at the level of which has been deposited a layer of encapsulating material 8, in a tank containing the sealing material 10.

Turning back now to the solvent used to permit the dissolution of the layer of resin 5, it preferably consists of acetone, namely when the resin 5 is formed of polymethyl methacrylate. However, this particular embodiment is not restrictive for the invention, and it is easily conceivable to use other solvents suitable for the dissolution of the resin 5, depending on the composition of the latter.

The method according to the present invention thus permits to obtain a nano-capsule 4 structure S including at least one nano-capsule 4 capable of permitting the encapsulation of a compound and including an encapsulating material 8, optionally filled with any compound 14, and sealed by means of a sealing material 10.

More particularly, the nanocapsule(s) 4 comprise at least one capsule 4 formed by a container 12 of a given depth p, equivalent to that of the cavity 7. Said container 12 includes a cover 13 formed of at least one layer of encapsulating material 8, and has an opening closed by a seal formed by the sealing material 10.

Preferably, the layer of encapsulating material 8 of said cover 13 has a thickness e that fulfils a given ratio p/e, with p corresponding to the depth of the container 12; thus, advantageously, p/e is higher than or equal to 2, preferably higher than 6 and even more preferably, p/e is higher than 10.

In FIG. 5B, the nano-capsule 4 structure S, which has been obtained and which is observed with a scanning electron microscope, includes nano-capsules 4 that have a depth p substantially equal to 330 nm and a thickness e in the range of 30 nm. Thus, the p/e ratio is approximately equal to 11.

FIG. 5C shows one single nano-capsule 4, also photographed with a scanning electron microscope. The depth p is in the range of 800 nm and the diameter is in the range of 300 nm. The seal formed by the sealing material 10, in this case the SU8 resin, is clearly visible in this figure.

The nano-capsules 4 encapsulating any compound are also schematically shown in FIG. 3D, when they are free in solution, and in FIG. 4, when they are associated with a second substrate 11.

In a particularly advantageous way, the depth p of the container 12 is between 20 nm and 1 µm, preferably between 50 and 500 nm and more preferably between 50 and 300 nm.

Indeed, by applying the method according to the invention, and namely by controlling the penetration of the beam during the step of structuring the layer of resin 5, it is easy to obtain a nano-capsule 4 the container 12 of which has the desired depth p, whereby the latter can vary depending on the compound 14 that can be encapsulated in said capsule 4.

As regards now the cover 13, it includes at least one layer of encapsulating material 8. The thickness e of a layer of encapsulating material 8 fulfils the following ratio: p/e higher than 2, preferably higher than 6 and preferably higher than 10.

When the cover 13 includes a plurality of layers of encapsulating material, each of the layers has a thickness e that fulfils the ratio p/e as defined in the preceding paragraph.

Preferably, the thickness of a layer of encapsulating material 8 is advantageously between 10 and 200 nm. Thus, the nano-capsules 4 of the structure S capable of permitting the encapsulation of a compound have a thin cover 13 including one or several layers of encapsulating material 8, eventually surrounding the encapsulated compound 14. This permits to effectively protect said compound 14, while facilitating its release at the appropriate time.

The nano-capsules 4 of the structure S, obtained by the implementation of the method according to the invention, have preferably a substantially cylindrical shape with a substantially round base. In this case, their diameter is varying and can be between 50 nm and a few microns. However, as illustrated in the attached figures, said nano-capsules 4 can also be slightly flared toward the portion of the resin 5 into contact with the layer of substrate 6, having then a shape close to that of a drop. The nano-capsules 4 of the structure S can also have any base, and namely of a triangular or rectangular shape.

The nano-capsule 4 structure S according to the invention is used namely for encapsulating a compound 14, whereby the latter can be any whatsoever. Depending on the nature of the compound 14, said nano-capsule 4 structure S can have various applications, in different fields.

As mentioned above in the description, the nano-capsules 4 of the structure S, which can encapsulate a compound 14, are likely to be released in solution, as illustrated in FIG. 3D. In another embodiment, namely shown in FIGS. 4, 5A and 5B, the nano-capsule 4 structure S can also be associated with a second substrate 11 after a step of transfer by bonding.

The nano-capsule 4 structure S according to the invention, including at least one nano-capsule 4, is particularly advantageous, namely because it permits a controlled release of the compound encapsulated in the nano-capsule(s) 4. This release can namely be obtained by applying, at the level of the nano-capsule 4 structure S, a means permitting the destruction of the cover 13 at a specific and chosen time. Such means can namely consist of an electric current or an electromagnetic field or an ultrasonic field or an electric field. Depending on the encapsulating material(s) 8 forming the cover 13 of the nano-capsule 4 structure S, such an application will cause a destruction and a break of said cover 13, which will result into a release of the compound 14 enclosed in the nano-capsule(s) 4 of the structure S.

In particular, when the encapsulating material 8 is formed of a piezoelectric material, the nano-capsule 4 structure S is subjected to an electric field, in order to cause a release of the encapsulated compound 14.

Advantageously, it is possible to use these means permitting a release of the compound 14, irrespective of the nano-capsule 4 structure S being associated with a substrate or the nano-capsules 4 being free in solution.

In the latter case, the nano-capsule 4 structure S can for example be transferred to the surface of a substrate 11 referred to as "intelligent", the intrinsic properties of which permit a conditional release of said encapsulated compound 14 when chemical and/or thermal and/or mechanical and/or biological stresses are applied to said intelligent substrate.

Figure 6:
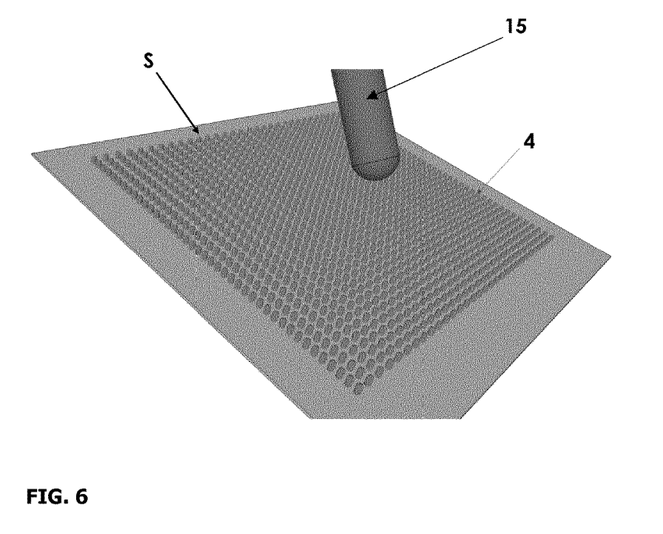
FIG. 6 is a schematic view, illustrating one of the possible applications of the nano-capsule structure according to the invention.

A first application of a nano-capsule 4 structure S according to the invention relates to the incorporation of a compound 14 such as a lubricant inside said structure S, within the nano-capsules 4. The latter can then be arranged on a surface requiring a permanent lubrication. Such a surface can namely consist of a safety system in a satellite, the latter being thus aimed at being used in a hostile environment, for example in the space, in which the lubricant compound quickly evaporates from the surface. In this particular application, illustrated schematically in the attached FIG. 6, the nano-capsule 4 structure S maintains the lubricant compound on the surface of the system, thus avoiding an evaporation of said compound in the space 14. Hence, the use of a nano-capsule 4 structure S according to the invention permits to guarantee an optimal lubrication, and over a long period of time, of the surface on which they are arranged. The release of the lubricant compound out of the nano-capsules 4 of the structure S can then be performed on command, for example by an apparatus 15, which can consist of a scraper, which results into a destruction of said nano-capsules 4 and a release of the compound on the surface to be lubricated.

According to a second particular application of the invention, the nano-capsule 4 structure S is intended for a biomedical application. In this case, the encapsulated compound 14 in the nano-capsules 4 consists of at least one active substance of a medicine 16. By active substance of a medicine are understood all the components of this drug having a therapeutic effect.

Figure 7:
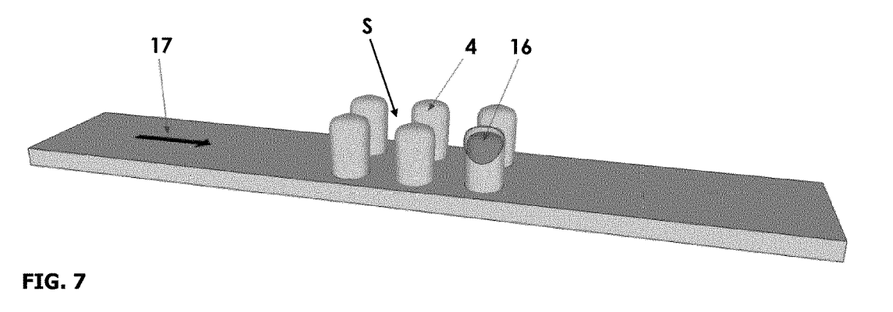
FIG. 7 is a schematic view, showing a second possible application of the nano-capsule structure.

In particular, in FIG. 7, an active substance 16 is encapsulated in the capsules 4 of a structure S arranged at the surface of a conductive substrate through which a current 17 circulates, resulting, through expansion and hyperthermia, into a release of said active substance 16 at the appropriate time. The flow of the current 17 in the conductive substrate thus permits a release on command of the encapsulated active substance 16.

Figure 8:
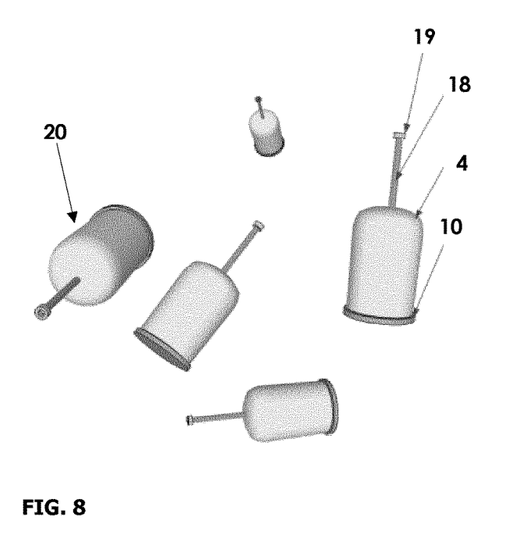
FIG. 8 is a schematic view, showing a third possible application of individual nano-capsules.

According to another particular embodiment, shown in FIG. 8, nano-capsules 4, obtained for example through release from a structure S including a plurality of capsules 4 and incorporating an active substance non visible in this figure, are coupled to a thiol-antigen sequence or a thiol-antibody sequence for a biomedical application. In this particular case, the encapsulating material 8, of which the nano-capsules 4 are formed, is preferably gold, platinum or tantalum, because of the biocompatibility of these metals. As regards the sealing material 10, it preferably consists of a biocompatible resin such SU8.

The thiol group 18 permits to perform the bonding between the nano-capsule 4 and the antibody or antigen 19. The latter can specifically target an undesirable cell present in the human body, namely a cancer cell. The complex 20, including the nano-capsule 4 and the thiol-antigen or antibody sequence, is thus fixed to the target cell to be eliminated. Said target cell, to which is specifically fixed the complex 20, is then destroyed by application of an electromagnetic field, for example. Indeed, such a field permits a disintegration of the nano-capsule 4, which also causes the destruction, by hyperthermia, of the target cell to which said capsule 4 is fixed through the thiol-antigen or antibody sequence. The so broken nano-capsule 4 then releases the active substance that will spread in the vicinity of the target cell that has been destroyed.

In a particularly advantageous way, the nano-capsules 4 according to the invention permit, in addition to facilitating the destruction of unwanted cells, to spread an active substance adapted at the level of the zone that has to be treated.

Many other applications, implementing the nano-capsule 4 structure S or the nano-capsules 4 according to the invention, can be considered.

For example, a structure S comprising a high density of nano-capsules 4 made of a metallic encapsulating material 8 permits to manufacture a mirror reflecting at any angle of incidence.

According to another embodiment, if the encapsulating material 8 used for manufacturing the nano-capsule 4 structure S consists of glass, and the encapsulated compound 14 consists of a gas, namely ozone ($O_3$), having the property of absorbing the ultraviolet rays, it is possible to manufacture mirrors reflecting certain wavelengths and absorbing other wavelengths.

In particular, such applications are possible when the nano-capsules 4 of the structure S have a curved geometry.

According to another application of the nano-capsule 4 structure S, when the nano-capsules 4 have a rectangular base, it is possible to manufacture laser structures. In particular, for this application, the encapsulated compound is preferably a gas, namely helium-neon (HeNe), and the nano-capsule 4 structure S is preferably formed of glass and metal.

In another interesting application of the nano-capsule 4 structures S according to the invention, the latter incorporate explosive materials or a combustion agent and a solution are dissolved in a fuel solution. This advantageously permits an increase of the thrust of the planes or the rockets.

The nano-capsule 4 structures S can also enclose a disinfecting product and a purifying product.

A nano-capsule 4 structure S according to the present invention can also serve as a support for producing nanowires formed of a material different from the one of said capsules 4. In particular, the nanowires can namely be made of gold and the nano-capsules 4 of aluminum. The nanowires are then obtained by evaporation of gold at 45° C.

and the nano-capsules 4 are then dissolved. It is then possible to obtain gold nanowires, which are releasable in solution.

It is also possible to use a nano-capsule 4 structure S according to the invention in particular applications permitting an energy generation and recovery.

Figure 9:
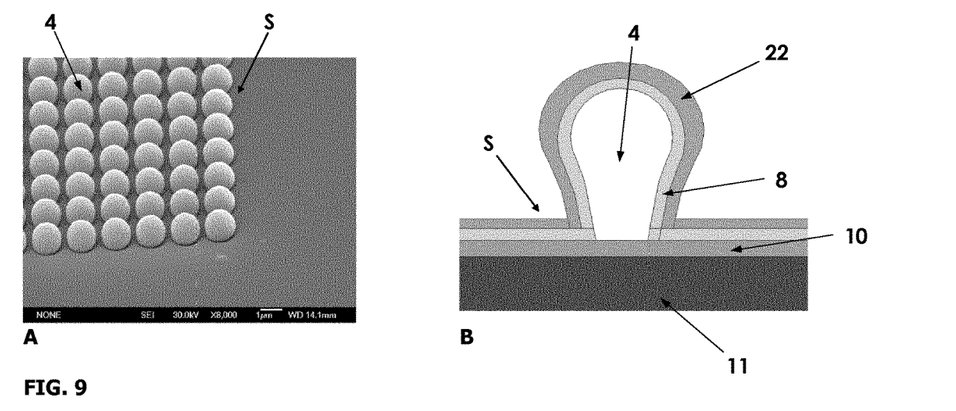
FIGS. 9A and 9B respectively show a photographic view, taken by a scanning electron microscope (magnification of 8000) and a schematic view of a representation of a fourth possible application of the nano-capsule structure obtained by implementing the method according to the invention.
Figure 10:
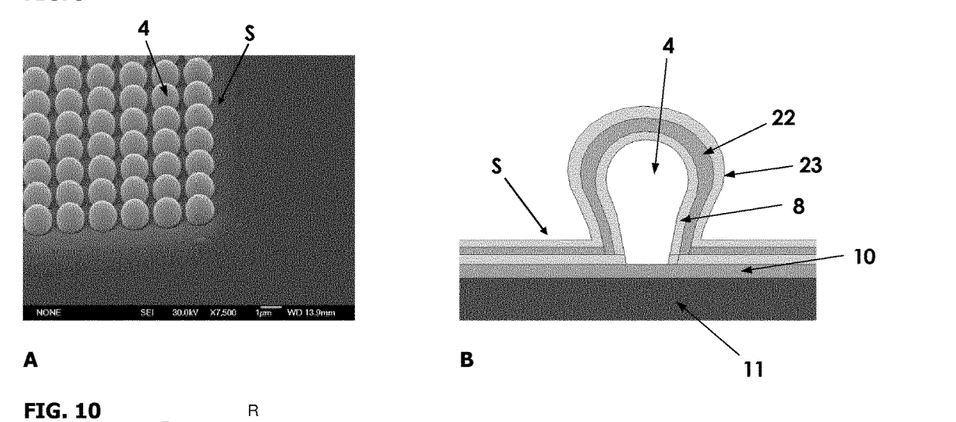
FIGS. 10A and 10B respectively show a photographic view taken by a scanning electron microscope (magnification of 7500) and a schematic view of a representation of a fifth possible application of the nano-capsule structure obtained by implementing the method according to the invention.

These applications are illustrated namely in FIGS. 9 and 10.

In FIG. 9B is a schematically illustrated a nano-capsule 4 of a nano capsule 4 structure S the cover of which includes a first metallic layer 8, for example aluminum and a second layer 22 of a piezoelectric material, for example zinc oxide.

However, it is possible to use other metal or piezoelectric materials that have already been detailed above.

FIG. 9A corresponds to a photograph taken with a scanning electron microscope of such a nano-capsule 4 structure S including a plurality of nano-capsules 4.

This nano-capsule 4 structure S shown in FIG. 9A can be achieved according to two approaches. The first one consists in spraying the two layers 8 and 22 by sputtering under vacuum following the structuring of the resin 5 in the cavities 7 obtained, and in transferring then the nano-capsule 4 structure S onto a second substrate 11 using either a sealing material 10 in order to permit the bonding of the structure S on said second substrate 11, or by using an adhesive resin, whereby the latter embodiment is not shown.

The second approach consists in spraying, once again using the technique of sputtering under vacuum, a first layer, in this case the metallic layer 8, then in carrying out the transfer onto a second substrate 11, and finally in spraying again, after the step of transferring, a layer 22 of piezoelectric material over the first metal layer 8. The second spraying is also a sputtering under vacuum.

FIGS. 10A and 10B illustrate a nano-capsule 4 structure S that can also be obtained by the two above-mentioned approaches for obtaining nano-capsule 4 structure S of FIG. 9, the nano-capsule 4 structure S of FIG. 10B including however an additional layer 23 that can for example consist of a layer of a metallic material.

The so obtained nano-capsule 4 structures S, including a layer of metal material 8 and a layer of piezoelectric material 22, or also two layers of metal 8 and 23 enclosing a layer of piezoelectric material 22, permit, when they are mechanically stressed, a generation of electricity.

Indeed, the piezoelectric materials have the capability of transforming a mechanical deformation into an electric field, and vice-versa. It is then possible, with the nano-capsule 4 structures S shown in FIGS. 9 and 10, to capture a mechanical deformation and to generate electricity.

Such nano-capsule 4 structures S can thus find an application in the manufacture of so-called "intelligent" clothes.

As regards in particular the nano-capsule 4 structure S shown in FIG. 10B, and having a cover including a layer 22 of piezoelectric material enclosed by two layers 8 and 23 of a metallic material, it can also permit to manufacture acoustic wave nano-resonators, the latter entering into resonance at their own frequency when they are subjected to an electric signal containing this frequency.

Indeed, the resonant frequency is inversely proportional to the thickness of the layer 22 of piezoelectric material. Therefore, a layer 22 having a thickness preferably between 10 and 200 nm permits to obtain resonance frequencies ranging from the gigahertz to the terahertz.

Such nano-resonators, which are miniature by nature, will find an interesting application in telecommunication systems, namely in the motor vehicle radars, or in the field of aviation, or also in the field of mobile telephony.

Figure 11:
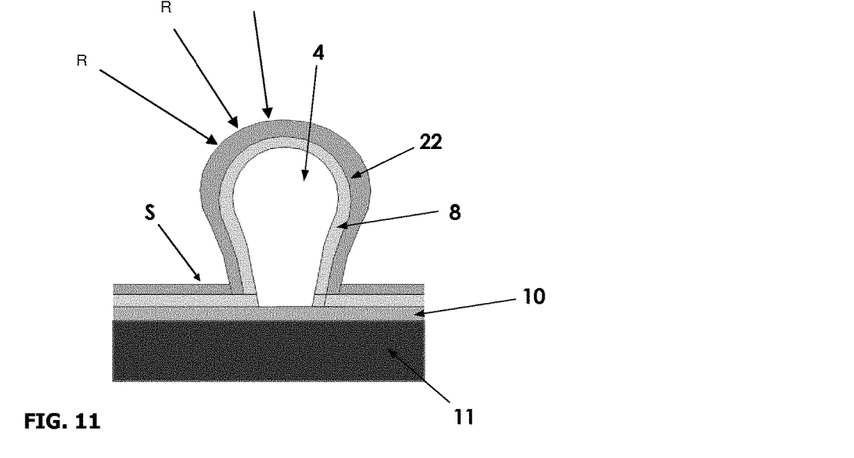
FIG. 11 is a schematic view of a sixth possible application of the nano-capsule structure obtained by implementing the present method.

FIG. 11 illustrates, in turn, an application of a nano-capsule 4 structure S obtained by implementing the method according to the invention in the field of optics.

More particularly, a nano-capsule 4 structure S that can be used in the field of optics has a first layer 8 of metallic material and a second layer of semiconductor material 22, such as namely zinc oxide.

A nano-capsule 4 structure S shown schematically in FIG. 11 can also be obtained by implementing the two approaches, namely:

spraying the two layers 8 and 22 after structuring the resin 5, then transferring onto a second substrate 11 through a layer 10 of sealing material or an adhesive resin not shown in FIG. 11;

or sputtering a first metal layer 8, transferring the nano-capsule 4 structure S onto a second substrate 11, then a new step of spraying a second layer 22 of semiconductor material onto the first metal layer 8.

The shape of the nano-capsule 4 structure S, and namely the curved geometry of the nano-capsules 4, coming close to that of a drop, permits to obtain a surface the photon absorption or emission of which is clearly improved. Indeed, irrespective of the angle of incidence of light rays on the nano-capsules 4, said rays (R), represented by the arrows (R, R, R) in FIG. 11, arrive on the surface of said nano-capsules 4 of the nano-capsule 4 structure S in normal incidence. This advantageously permits to avoid the reflections on the surface when the angle of incidence is not normal to the plane.

When a layer of semiconductor material 22 covers the nano-capsule 4 structure S, it is possible to obtain a photo-diode-like absorbent surface, irrespective of the angle of incidence of the rays, or a transmitting surface in omnidirectional transmission.

Indeed, the semiconductor materials are capable of interacting with the light, namely with light photons and with the electrons. It is then possible to manufacturing, with a nano-capsule 4 structure S having a first layer 8 of metallic material and a second layer 22 of semiconductor material, a photodiode capable of receiving the photons and of generating electricity.

The use of such nano-capsule 4 structures S therefore permits a considerable improvement in efficiency of the solar panels.

It can also be considered to manufacture an omnidirectional optical source, such as a light-emitting diode or a laser, capable of capturing the electrons and of generating photons, thus of emitting light.

Eventually, for such applications, the nano-capsule structure S includes, in addition to the two above-mentioned layers 8 and 22, a third layer formed of a metallic material, not shown in FIG. 11, enclosing the layer 22 of semiconductor material with the first metallic layer 8.

What is claimed:

1. A method for obtaining at least one nano-capsule structure, wherein at least one capsule encapsulates a compound, said method comprising the following steps:

depositing at least one layer of resin having a thickness between 300 nm and 2 microns on a layer of substrate;

structuring said layer of resin by one of a group consisting of: low-voltage electron lithography, optical lithography and nanoimprinting;

forming at least one cavity in said thickness of said layer of resin, the cavity having a depth of 20-450 nm;

sputtering an encapsulating material under vacuum so as to form an isotropic deposition of at least one layer of said encapsulating material;

sealing the cavity with a sealing material so as to form at least one capsule; and dissolving said layer of resin by soaking into a suitable solvent.

2. The method, according to claim 1, further comprising the step of:

filling the cavity with a compound, after the step of sputtering the encapsulating material, said compound being one of a group consisting of: liquid, solid, and vacuum.

3. The method, according to claim 1, wherein the structuring of the layer of resin is by low-voltage electron lithography between 1 and 15 kV.

4. The method, according to claim 3, further comprising the step of:

performing an iterative approach test, before the step of structuring of the layer of resin, so as to determine an electron dose to be sent to the layer of resin and avoid a piercing of the layer of resin down to the layer of substrate.

5. The method, according to claim 1, wherein the layer of resin is deposited by spin coating on the layer of substrate.

6. The method, according to claim 1, wherein the step of sputtering an encapsulating material is carried out at a power between 80 and 120 Watts.

7. The method, according to claim 1, wherein temperature is controlled between 15° C. and 30° C.

8. The method, according to claim 1, wherein at least one layer of encapsulating material is sprayed, the least one layer having a thickness between 10 and 200 nm.

9. The method, according to claim 1, wherein said resin is one of a group consisting of polymethyl methacrylate, polymethyl methacrylate methacrylic acid, and a mixture of polymethyl methacrylate and polym ethyl methacrylate methacrylic acid.

10. The method, according to claim 1, wherein the substrate is a material selected from a group consisting of silicon, zinc oxide, aluminum nitride, oxide silicon, aluminum oxide, polymers, and plastic materials.

11. The method, according to claim 1, wherein said encapsulating material is selected from a group consisting of metallic materials, semiconductor materials, piezoelectric materials and insulating materials.

12. The method, according to claim 1, wherein said sealing material is selected from a group consisting of: polymers, metals, epoxy resins and biocompatible resins, said sealing material withstanding the solvent in the step of dissolving the layer of resin.

13. The method, according to claim 1, further comprising the steps of:

applying an adhesive resin onto a surface of said sealing material, prior to the step of dissolving the layer of resin; and depositing a second substrate on said adhesive resin, wherein said at least one capsule is attached to said second substrate, after the step of dissolving the layer of resin, said at least capsule being transferred from said layer of substrate to said second substrate.

14. The method, according to claim 1, further comprising the step of:

depositing a second substrate on a surface of sealing material, prior to the step of dissolving the layer of resin, wherein said at least one capsule is attached to said second substrate, after the step of dissolving the layer of resin, said at least capsule being transferred from said layer of substrate to said second substrate.

15. The method, according to claim 13, further comprising the step of:

sputtering at least a second layer selected from a group consisting of a metallic, semiconductor, piezoelectric, and insulating material, on the layer of encapsulating material when said at least one capsule is attached to said second substrate, after the step of dissolving the layer of resin.

16. The method, according to claim 1, following the step of sealing the cavity, the method further comprising the steps of:

structuring the layer of sealing material, through alignment with first structuring of the layer of resin, by one of a group consisting of: electron lithography, optical lithography, and nanoimprinting, so as to remove the sealing material, except at a level of the nano-capsule to remain sealed;

removing the layer of encapsulating material by one of a group consisting of: chemical etching, soaking, reactive ion etching, and ion beam etching;

after the step of dissolving the layer of resin, releasing said nano-capsule in solution.

\* \* \* \* \*